(12) United States Patent
Furst et al.

(10) Patent No.: US 6,245,028 B1
(45) Date of Patent: Jun. 12, 2001

(54) NEEDLE BIOPSY SYSTEM

(75) Inventors: Daniel S. Furst, Concord; Shalabh Chandra, Mayfield Heights; Dominic J. Heuscher, Aurora; Raj Shekhar, Mayfield Heights, all of OH (US)

(73) Assignee: Marconi Medical Systems, Inc., Highland Heights, OH (US)

( * ) Notice: Subject to any disclaimer, the term of this patent is extended or adjusted under 35 U.S.C. 154(b) by 0 days.

(21) Appl. No.: 09/449,322

(22) Filed: Nov. 24, 1999

(51) Int. Cl.$^7$ .................................................. A61B 10/00
(52) U.S. Cl. ............................................. 600/568; 600/411
(58) Field of Search .................................... 600/411, 416, 600/417, 562, 564, 568; 606/130; 414/1, 5; 434/262

(56) References Cited

U.S. PATENT DOCUMENTS

| | | | |
|---|---|---|---|
| 5,762,458 | * 6/1998 | Wang et al. ............................. | 414/1 |
| 5,876,325 | * 3/1999 | Mizuno et al. ...................... | 600/102 |
| 5,882,206 | * 3/1999 | Gillio .................................. | 434/262 |
| 6,001,108 | * 12/1999 | Wang et al. ......................... | 606/130 |
| 6,074,213 | * 6/2000 | Hon ..................................... | 434/262 |
| 6,094,590 | * 7/2000 | Kan et al. ............................. | 600/411 |
| 6,102,850 | * 8/2000 | Wang et al. ......................... | 600/102 |
| 6,113,395 | * 9/2000 | Hon ..................................... | 434/262 |

* cited by examiner

*Primary Examiner*—Eric F. Winakur
*Assistant Examiner*—Charles Marmor, II
(74) *Attorney, Agent, or Firm*—Fay, Sharpe, Fagan, Minnich & McKee, LLP

(57) ABSTRACT

A needle biopsy system (10) includes a biopsy needle (210), and a needle support assembly (200). The needle support assembly (200) holds the biopsy needle (210) and manipulates the biopsy needle (210) in response to received control signals. A needle simulator (250) having an input device (252) generates the control signals in response to manipulation of the input device (252) by an operator. The operator, in turn, receives feedback from the needle simulator (250) in accordance with forces experienced by the biopsy needle (210). In a preferred embodiment, the feedback received by the operator includes tactile sensations experienced by the operator as the operator manipulates the input device (252). The tactile sensations mimic those the operator would have received had the operator directly manipulated the biopsy needle (210). Optionally, a curved needle guide (280) is employed to restrict the biopsy needle's progression longitudinally therethrough.

20 Claims, 4 Drawing Sheets

NEEDLE BIOPSY SYSTEM

BACKGROUND OF THE INVENTION

The present invention relates to minimally invasive surgical systems and methods. It finds particular application in conjunction with image-guided needle biopsies performed using continuous computed tomography (CCT) scanning or other similar imaging systems, and will be described with particular reference thereto. However, it is to be appreciated that the invention is also applicable to other imaging modalities and other biopsy surgical techniques.

It is often desirable to sample or test a portion of tissue from human or animal subjects, particularly in the diagnosis and treatment of potentially cancerous tumors, premalignant conditions, and other diseases or disorders. Typically, in the case of tumors, when the physician suspects that cancer or an otherwise diseased condition exists, a biopsy is performed to determine if in fact cells from the tumor are cancerous or otherwise diseased. Many biopsies, such as percutaneous biopsies, are performed with a needle-like instrument used to collect the cells for analysis.

In recent years, the performance of needle biopsies has been enhanced by the use of x-ray and computed tomography (CT) scans. The imaging equipment allows an interventionalist, such as a radiologist, surgeon, physician, or other medical personnel, to track the insertion of interventional devices, such as biopsy needles, in a subject during diagnostic and therapeutic procedures. While such imaging modalities are helpful to the interventionalist and the patient, they have certain drawbacks.

For example, with such image-guided procedures, the tracking of needle position is not done in real-time. That is to say, a static image is obtained and the needle position noted therein. Subsequently, the needle is advanced or retracted by a small amount and another static image obtained to verify the new needle position. This sequence is repeated as many times as necessary to track the needle's progression. Such a procedure tends to be time consuming insomuch as the needle progresses by only a short distance or increment between imaging, and needle progression is halted during imaging. Moreover, accuracy suffers to the extent that in the interim, i.e., between images, the needle's position cannot be visualized.

With the development of CCT imaging and fluoroscopy, real-time imaging has been made possible. In CCT scanning, a rotating x-ray source irradiates the subject continuously, generating images at a rate of approximately six frames per second. The use of CCT or fluoroscopy by the interventionalist for real-time guidance and/or tracking of the needle during biopsies is gaining popularity. As a result, biopsies have become not only more accurate, but also shorter in duration.

However, a problem resides in protecting the interventionalist from radiation exposure. In needle biopsies, for example, often the biopsy needle and guide are held within or close to the plane of the x-ray radiation so that the needle-tip will reside in the image plane thereby permitting continuous tracking. Staying close to the plane of imaging also, more often than not, allows for the distance the needle passes through the subject to be minimized. Consequently, this typically results in the interventionalist placing his/her hands in the x-ray beam. The hands of an interventionalist who performs several such procedures per day can easily receive a toxic dose of radiation. Therefore, it is desirable to provide interventionalists with a way to perform needle biopsies using CCT scanning without the risk of radiation exposure.

One proposed approach involves the use of a mechanical system which allows the interventionalist to manipulate the biopsy needle while his hands remain clear of the x-ray beam. However, such systems with mechanical linkages reduce or eliminate the tactile sensations (e.g., force, shear, and/or moment on the needle) otherwise available to an interventionalist directly manipulating the needle. This is disadvantageous in that interventionalists typically obtain useful information regarding the procedure from these tactile sensations. For example, they are often able to feel the needle transition between different tissue types, contact with bones, etc. The interventionalist generally desire this "feel" as they perform biopsies. To trained personnel, it serves as an additional indication of the needle's location.

The present invention provides a new and improved system and technique for performing a needle biopsy that overcomes the above-referenced problem and others.

SUMMARY OF THE INVENTION

In accordance with one aspect of the present invention, a needle biopsy system includes a biopsy needle and a needle support assembly. The needle support assembly holds the biopsy needle and manipulates the biopsy needle in response to received control signals. A needle simulator using an input device generates the control signals in response to manipulation of the input device by an operator. The operator, in turn, receives feedback from the needle simulator in accordance with forces experienced by the biopsy needle.

In accordance with a more limited aspect of the present invention, the feedback received by the operator includes tactile sensations experienced by the operator as he manipulates the input device. The tactile sensations mimic those that the operator would have received had he directly manipulated the biopsy needle.

In accordance with a more limited aspect of the present invention, the needle biopsy system further includes a force measuring transducer associated with the needle support assembly for measuring forces experienced by the biopsy needle.

In accordance with a more limited aspect of the present invention, the force measuring transducer includes a load cell connected to the biopsy needle. The load cell generates force signals in response to detected forces acting on the biopsy needle. The force signals are then relayed to the needle simulator.

In accordance with a more limited aspect of the present invention, the load cell also generates moment signals in response to detected moments acting on the biopsy needle. The moment signals are then relayed to the needle simulator.

In accordance with a more limited aspect of the present invention, the needle biopsy system further includes a needle guide attached to the needle support assembly. The needle guide is a hollow shaft dimensioned to receive the biopsy needle such that it freely progresses longitudinally there through while being restricted in its lateral movement.

In accordance with a more limited aspect of the present invention, the hollow shaft is curved.

In accordance with a more limited aspect of the present invention, the biopsy needle is connected to the needle support assembly via a quick release coupling arranged so that the biopsy needle is readily detachable from the needle support assembly.

In accordance with a more limited aspect of the present invention, the quick release coupling automatically releases the biopsy needle from the needle support assembly upon application of an amount of force thereto in excess of a determined level.

In accordance with a more limited aspect of the present invention, prior to the needle support assembly manipulating the biopsy needle, the control signals are filtered to compensate for unwanted manipulations of the input device by the operator.

In accordance with a more limited aspect of the present invention, the needle biopsy system further includes an image guidance system. The image guidance system is a medical diagnostic imager having a human viewable display which is employed to visualize procedures.

In accordance with a more limited aspect of the present invention, the biopsy needle system further includes an indicator panel having at least one operator perceivable visual and/or audible signal controlled in response to the forces experienced by the biopsy needle.

In accordance with another aspect of the present invention, a method for performing a needle biopsy on a subject is provided. The method includes adjusting a needle support assembly which holds a biopsy needle such that the biopsy needle is positioned relative to the subject at a desired insertion point and orientation. Thereafter, an input of a needle simulator remote from the needle support assembly is manipulated in order to affect a desired manipulation of the biopsy needle. A needle control signal is generated in response to the manipulation of the input of the needle simulator. The needle control signal is then relayed to the needle support assembly, and the desired manipulation of the biopsy needle is produced in response to the needle control signal. A force on the biopsy needle is sensed, and a force signal is generated in response to the sensed force on the biopsy needle. Next, the force signal is relayed to the needle simulator, and tactile feedback is applied to the input of the needle simulator in response to the force signal.

In accordance with a more limited aspect of the present invention, the tactile feedback mimics tactile sensations which would have been felt by the medical professional had he been manipulating the biopsy needle directly.

In accordance with a more limited aspect of the present invention, between the steps of generating a needle control signal and producing the desired manipulation, the method further includes filtering the control signal to compensate for unwanted components of the manipulation of the input of the needle simulator.

In accordance with a more limited aspect of the present invention, during the needle biopsy, the method further includes obtaining medical diagnostic images of a region of interest of the subject. The region of interest has the biopsy needle located therein.

In accordance with a more limited aspect of the present invention, the method further includes providing a human perceivable signal in response to the force signal.

In accordance with a more limited aspect of the present invention, the human perceivable signal is an alarm which is triggered when the force signal crosses a determined threshold.

In accordance with another aspect of the present invention, an image-guided needle biopsy system includes a CCT imaging unit having a subject support for suspending a subject at least partially within an examination region. It also includes a biopsy needle and a mechanical needle biopsy system. The mechanical needle biopsy system includes a robotic arm adjustably mounted to the subject support. The robotic arm inserts and retracts the biopsy needle into and out of the subject and senses forces acting on the biopsy needle. A needle guide directs the biopsy needle there through. The needle guide is detachably mounted to the robotic arm. An included haptic needle simulator is manipulated in order to control the biopsy needle remotely. The haptic needle simulator reflects sensed forces acting on the biopsy needle to an interventionalist manipulating the haptic needle simulator.

In accordance with a more limited aspect of the present invention, the biopsy needle is flexible and the needle guide is curved.

In accordance with a more limited aspect of the present invention, the biopsy needle is detachably coupled to the robotic arm.

One advantage of the present invention is that it provides a safe environment for interventionalists to perform needle biopsies with real-time image guidance.

Another advantage of the present invention is that interventionalists have available information from the tactile sensations associated with the needle biopsy.

Yet another advantage of the present invention is that it provides a more sterile environment for needle biopsies.

Still another advantage of the present invention is that it provides a more convenient and comfortable environment for the interventionalist when performing a biopsy or other like procedure, i.e., rather than awkwardly leaning over the patient.

Yet another advantage of the present invention is that it provides for "tele-biopsy" procedures from remote locations.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
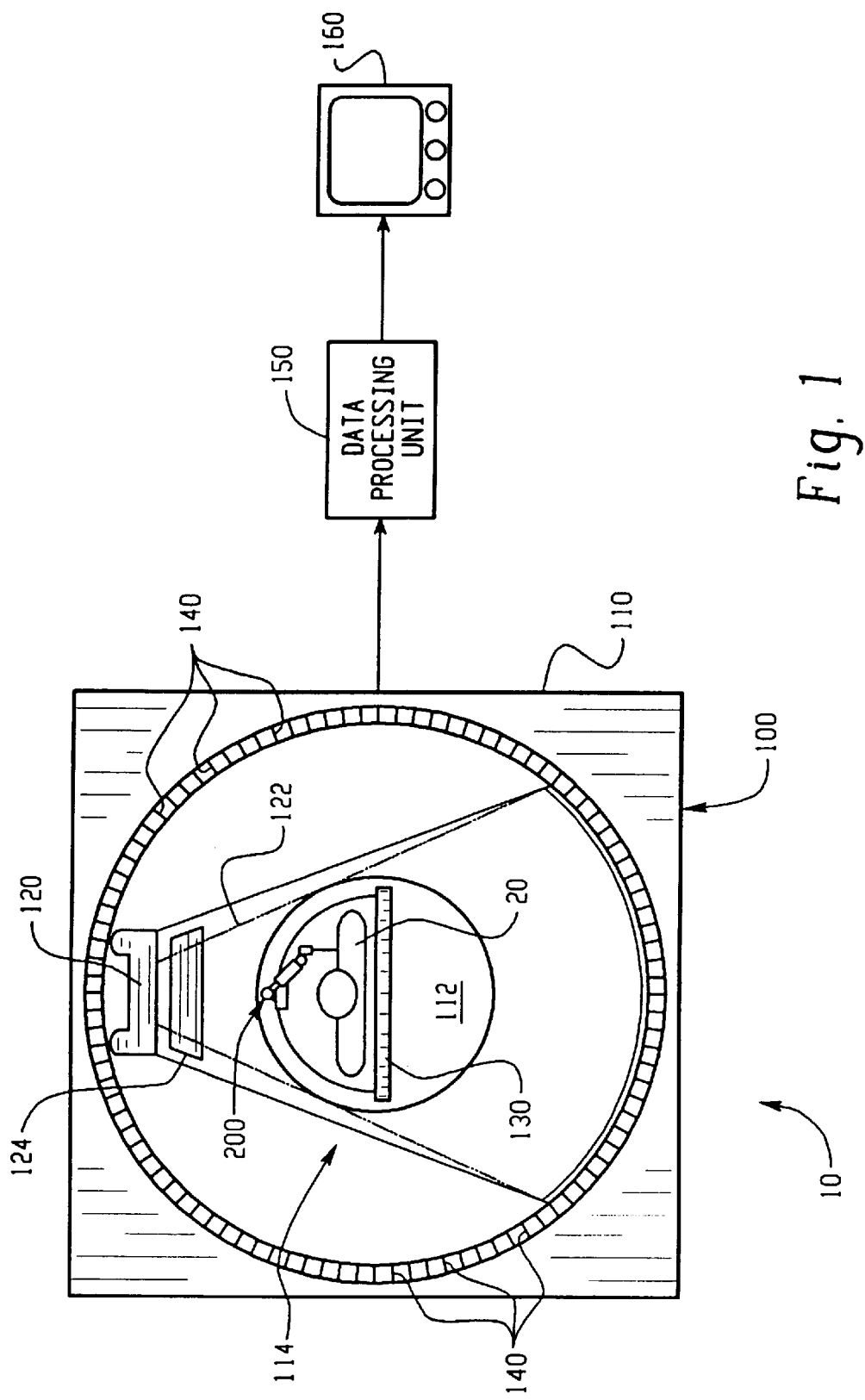
FIG. 1 is a diagrammatic illustration of an image-guided needle biopsy system in accordance with aspects of the present invention.

With reference to FIG. 1, an image-guided needle biopsy system 10 includes a diagnostic imaging apparatus 100 capable of generating continuous medical diagnostic images of a subject 20 updated in real-time or at close temporal intervals, six images per second in a preferred embodiment.

In a preferred embodiment, the diagnostic imaging apparatus 100 includes a CT scanner having a stationary gantry 110 which defines a central examination region 112. A rotating gantry 114 is mounted on the stationary gantry 110 for rotation about the examination region 112. A source of penetrating radiation 120, such as an x-ray tube, is arranged on the rotating gantry 114 for rotation therewith. The source of penetrating radiation produces a beam of radiation 122 that passes through the examination region 112 as the rotating gantry 114 rotates. A collimator and shutter assembly 124 forms the beam of radiation 122 into a thin fan-shape and selectively gates the beam 122 on and off. Alternately, the radiation beam 122 is gated on and off electronically at the source 120. Nevertheless, the source 120 remains on for the duration of a continuous imaging scan. Using an appropriate reconstruction algorithm in conjunction with the data acquired from the CT scanner, images are continuously reconstructed and updated at 6 frames a second. This mode of operation of the scanner is called the CCT mode.

A subject support 130, such as an operating table, couch or the like, suspends or otherwise holds the subject 20 received thereon, such as a human or animal patient, at least partially within the examination region 112 such that the thin fan-shaped beam of radiation 122 cuts a cross-sectional slice through the region of interest of the subject 20.

In the illustrated fourth generation CT scanner, a ring of radiation detectors 140 is mounted peripherally around the examination region 112 on the stationary gantry 110. Alternately, a third generation CT scanner is employed with an arc of radiation detectors 140 mounted on the rotating gantry 114 on a side of the examination region 112 opposite the source 120 such that they span the arc defined by the thin fan-shaped beam of radiation 122. Regardless of the configuration, the radiation detectors 140 are arranged to receive the radiation emitted from the source 120 after it has traversed the examination region 112.

In a source fan geometry, an arc of detectors which span the radiation emanating from the source 120 are sampled concurrently at short time intervals as the source 120 rotates behind the examination region 112 to generate a source fan view. In a detector fan geometry, each detector is sampled a multiplicity of times as the source 120 rotates behind the examination region 112 to generate a detector fan view. The paths between the source 120 and each of the radiation detectors 140 are denoted as rays.

The radiation detectors 140 convert the detected radiation into electronic projection data. That is to say, each of the radiation detectors 140 produces an output signal which is proportional to an intensity of received radiation. Optionally, a reference detector may detect radiation which has not traversed the examination region 112. A difference between the magnitude of radiation received by the reference detector and each radiation detector 140 provides an indication of the amount of radiation attenuation along a corresponding ray of a sampled fan of radiation. In either case, each radiation detector 140 generates data elements which correspond to projections along each ray within the view. Each element of data in the data line is related to a line integral taken along its corresponding ray passing through the subject being reconstructed.

The image data from the radiation detectors 140 is collected and reconstructed into an image representation of the subject 20 in the usual manner. For example, a data processing unit 150 collects the image data and reconstructs the image representation therefrom using rebinning techniques, convolution/backprojection algorithms, and/or other appropriate reconstruction techniques. In a preferred embodiment, the image representation, corresponding to the cross-sectional slice traversed by the thin fan-shaped beam of radiation 122 through the region of interest of the subject 20, is displayed on a human viewable display, such as a video monitor 160 or the like. Preferably, during operation in the CCT scan mode, the image representation is updated at a rate of approximately 6 frames per second or more. In this manner then, an interventionalist performing a biopsy is able to track needle progression in real-time by viewing the image representation displayed on the video monitor 160.

Figure 2:
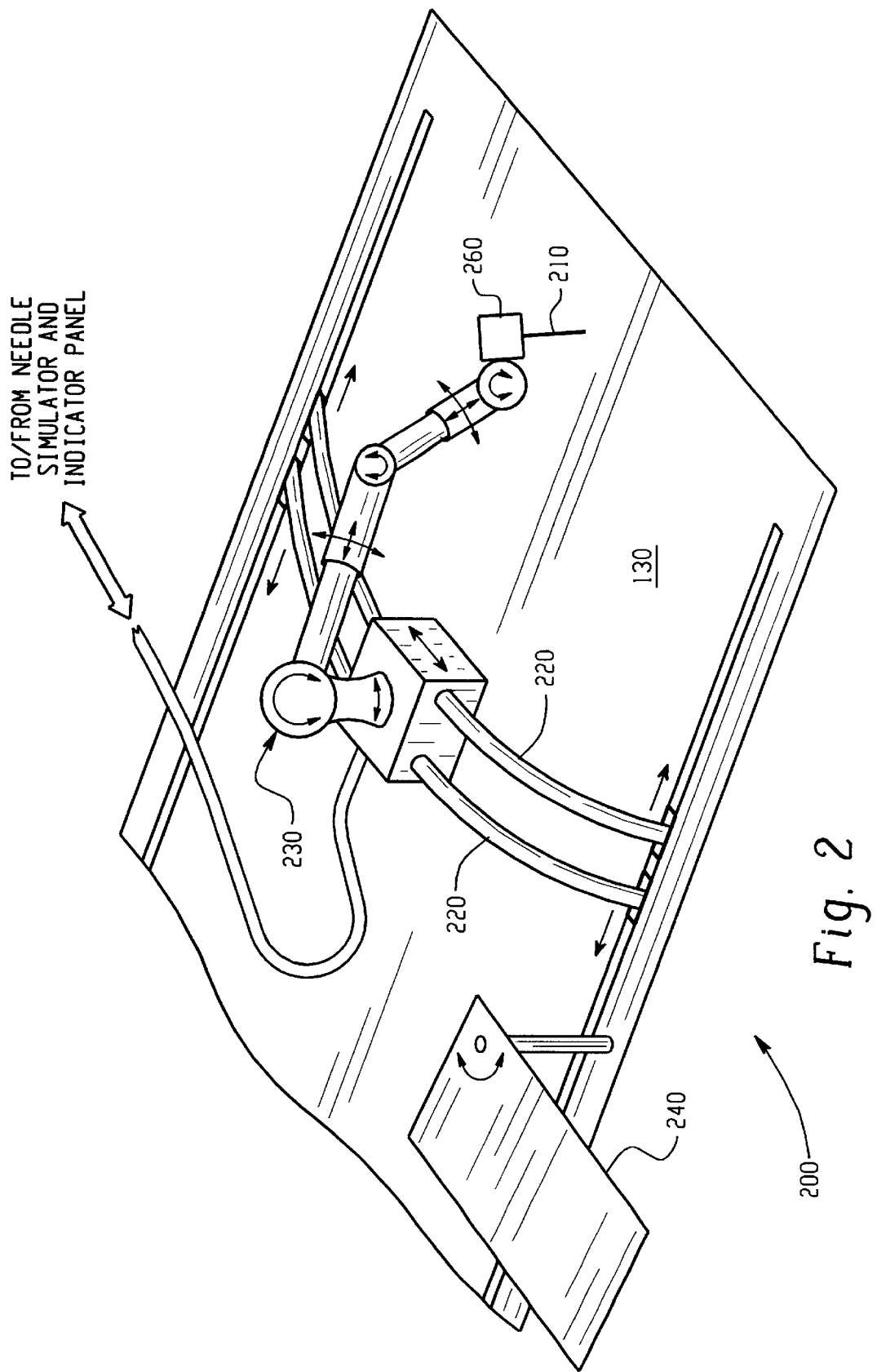
FIG. 2 is a diagrammatic illustration of a needle support assembly in accordance with aspects of the present invention.

With reference to FIG. 2 and continuing reference to FIG. 1, in a preferred embodiment, the image-guide needle biopsy system 10 also includes a mechanical needle support assembly 200 which holds a biopsy needle 210 at a desired location and trajectory. The mechanical needle support assembly 200 optionally includes an arch support assembly 220 and a needle support arm 230. The arch support assembly 220 preferably comprises substantially rigid members extending in an arch from one side of the subject support 130 to the other leaving clearance for the subject 20 thereunder. Optionally, the arch support assembly 220 is height adjustable. In a preferred embodiment, the arch support assembly 220 is attached to the subject support 130 on either side via longitudinally extending guides, tracks, or the like, along which the arch support assembly 220 is selectively positioned and/or fixed as desired. Likewise, the arch support assembly 220 serves as a laterally extending guide or track along which a first end of the needle support arm 230 is selectively positioned and/or fixed as desired.

The needle support arm 230 is preferably a fully adjustable multi-jointed multi-segmented arm with each joint having varying degrees of freedom (optionally, universal or ball type joints) and each segment being selectively expandable and retractable. As will be described in greater detail later herein, the biopsy needle 210 is held and/or otherwise attached to an end opposite the first end of the needle support arm 230. Accordingly, by appropriately selecting the longitudinal position of the arch support assembly 220 along the subject support 130, and appropriately selecting the lateral position of the needle support arm 230 along the arch support assembly 220, and flexing or otherwise adjusting the multiple joints and/or segments of the needle support arm 230, any arbitrary position and/or orientation of the biopsy needle 210 relative to the subject 20 is achieved as desired.

Figure 3:
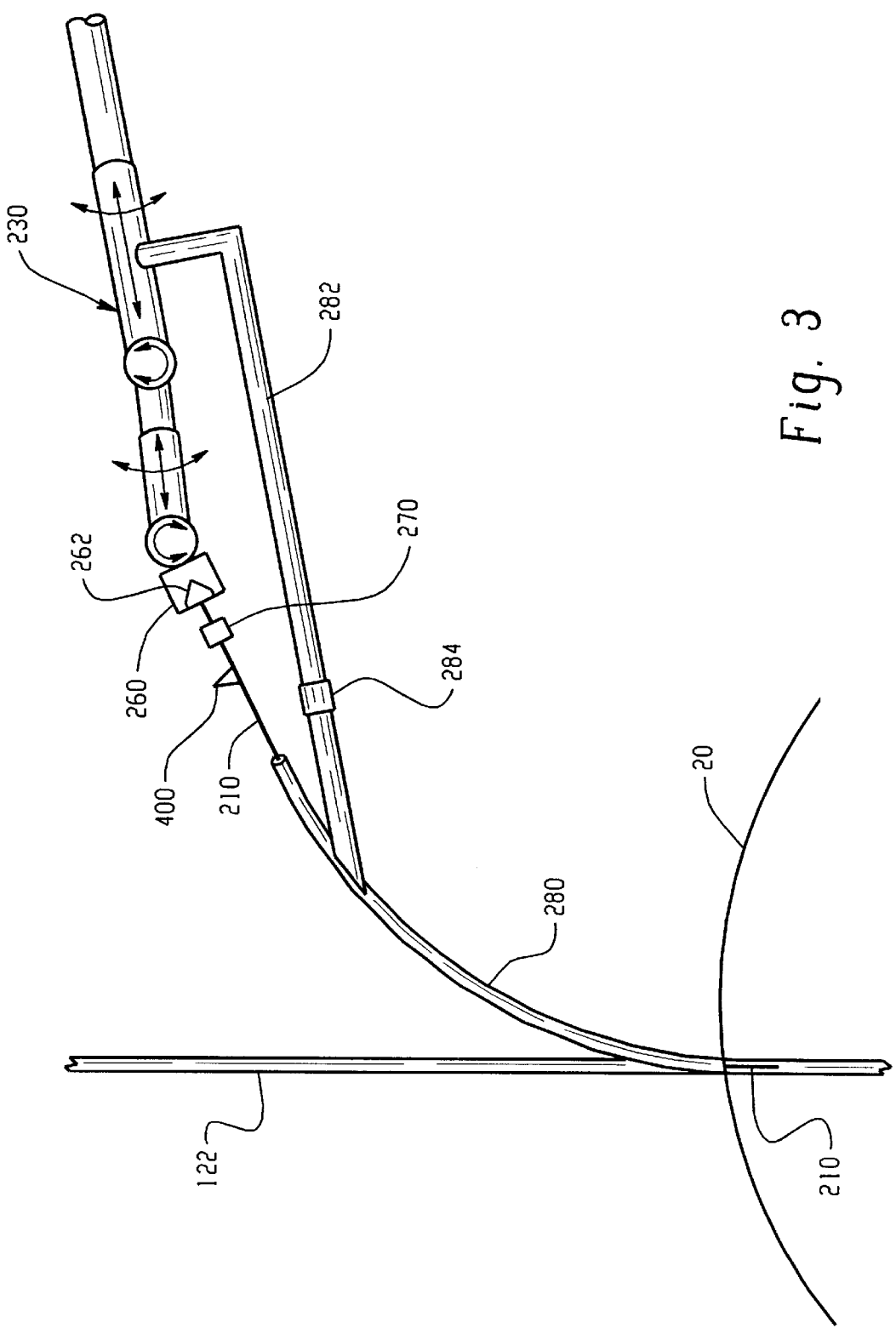
FIG. 3 is a diagrammatic illustration of a needle support arm with needle guide in accordance with aspects of the present invention.

With reference to FIG. 3 and continuing reference to FIGS. 1 and 2, performance of the biopsy preferably begins with adjusting the mechanical needle support system 200 so that the biopsy needle 210 is initially set at the desired insertion location and oriented along the desired trajectory. So that the biopsy needle's location is visualized throughout its entire progression, and to minimize the distance the biopsy needle 210 travels through the subject 20, the trajectory preferably resides in the plane of the beam of radiation 122. The biopsy needle 210 is initially set by sliding or otherwise positioning the needle support arm 230 laterally along the arch support assembly 220 and sliding or otherwise positioning the arch support assembly 220 longitudinally along the subject support 130. The arch support assembly 220 and the needle support arm 230 together provide complete freedom for the positioning and orienting of the biopsy needle 210. After initial positioning and during the needle biopsy procedure, the CT scanner is employed in the CCT mode to image the region of interest (i.e. the plane of the thin fan-shaped beam of radiation 122) with the biopsy needle 210 therein.

Optionally, in an alternative embodiment, the biopsy needle 210 is automatically positioned. That is to say, the medical professional or other operator maps out the procedure by identifying the location of a tumor in a prior obtained image and a desired angle of needle insertion. In response, the mechanical needle support system 200 automatically (via mechanical drivers and relative position sensors) locates the biopsy needle 210 at the appropriate position for performing the mapped procedure.

Optionally, adjustable biopsy tables 240 may be attached to the subject support 130 for convenience during the procedure. These tables 240, which are outside of the beam of radiation 122, are used to support or otherwise hold and make readily available additional components (as discussed elsewhere herein) of the image-guided needle biopsy system 10, surgical and interventional tools, and/or other instruments used by the interventionalist during the procedure. Additionally, the biopsy tables 240 are optionally swung into position over the subject 20 so that the interventionalist can support and/or steady his hand or body therefrom in cases where it is desired to manually perform the biopsy, either partially or in its entirety.

Figure 4:
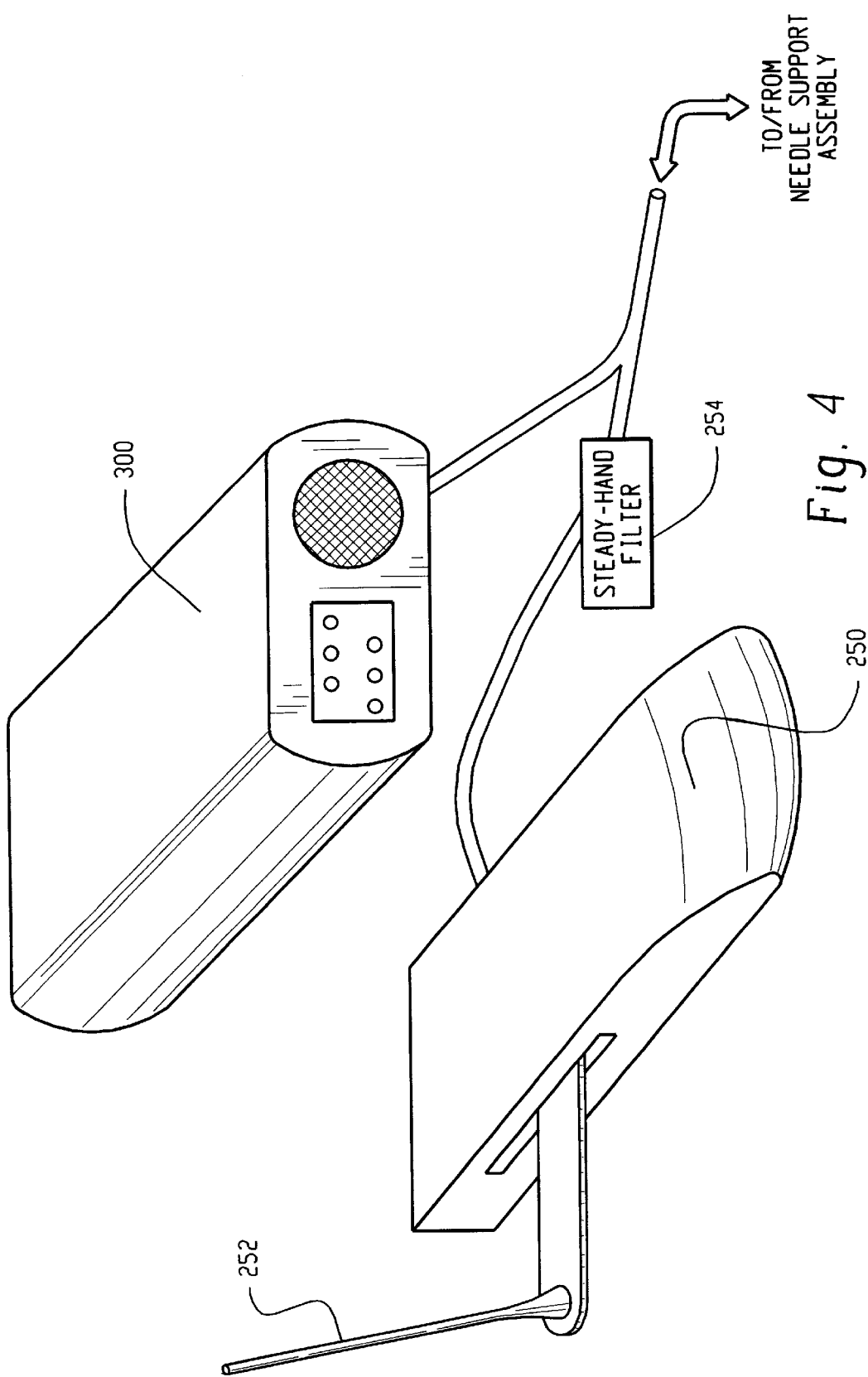
FIG. 4 is a diagrammatic illustration of a haptic needle simulator and indicator panel in accordance with aspects of the present invention.

With reference to FIG. 4 and continuing reference to FIGS. 1 through 3, in a preferred embodiment, the image-guided needle biopsy system 10 further includes a remote haptic needle simulator 250 which has a joystick 252 or other asuch input device that is physically manipulated by the interventionalist to, in turn, manipulate and/or control the actual biopsy needle 210. Preferably, the needle support arm 230 is a robotic arm whose multiple joints flex or otherwise rotate and segments expand or retract in accordance with control signals received from the haptic needle simulator 250. The control signals generated by the haptic needle simulator 250 are such that the action of the needle support arm 230 mimics, either directly or by a scaled amount, the interventionalist's physical manipulation of the joystick 252. These control signals are relayed from the remotely located haptic needle simulator 250 to the needle support arm 230 optionally via physical cable or in a wireless fashion using an infrared link, radio communication, or the like. In this manner then, the remote nature of the haptic needle simulator 250 allows it to be arbitrarily positioned. Accordingly, to the degree desired, the interventionalist is kept clear of the radiation.

Prior to being relayed to the needle support arm 230, the control signals are optionally filtered by a steady-hand filter 254. Alternately, the steady-hand filter 254 operates on the receiving end and is incorporated with the needle support arm 230. In either case, the steady-hand filter 254 removes, smooths out, or otherwise filters, from the control signals, noise or signal components which are a result of an interventionalist's hand tremors. Consequently, slightly unstable and/or unwanted displacements of the biopsy needle 210 do not result from these hand tremors. Filtering out hand tremor noise provides for a more stable and accurate needle biopsy. Additionally, the steady-hand filter 254 prevents sudden, sharp movement of the biopsy needle 210. This feature is important in the case of a slip or flinch by the interventionalist. Such a sharp and unintentional movement is potentially harmful to the subject 20. That is to say, the steady-hand filter 254 "catches" such an unintentional hand movement and blocks the control signal from causing a resultant displacement of the biopsy needle 210. Optionally, other signal or data processing as appropriate is also performed prior to the needle support arm 230 responding to the control signals.

A force and moment measuring assembly 260, preferably comprising a load cell which contains pressure and moment transducers, or other such force/moment measuring devices, which record or otherwise measure the forces and/or moments experienced by the biopsy needle 210 as it is manipulated. Preferably, the force measuring assembly 260 is held by, attached to, or otherwise incorporated with the end of the needle support arm 230. The biopsy needle 210 is, in turn, connected to a force/moment sensing input 262 of the measuring assembly 260. The force/moment measuring assembly 260 generates force and moment signals in response to the forces and moments sensed by the force/moment sensing input 262 which result from the forces and moments experienced by the connected biopsy needle 210. In its preferred embodiment, the force and moment measuring assembly 260 comprises a single load cell which generates a corresponding signal in response to all the forces and moments (i.e., in and/or about three orthogonal directions) experienced by the biopsy needle 210 which is connected to the load cell's input 262. This allows for the measuring of shear and transverse forces along with the axial force experienced by the biopsy needle 210. However, in alternate embodiments, optionally, the biopsy needle 210 is mechanically linked to one or more load cells which each measures a single shear, transverse, or axial force or moment. In any event, it is preferred that the biopsy needle 210 be attached to the force and moment measuring assembly 260 via a quick release connection or coupling 270 so that, if the interventionalist desires to proceed manually, the biopsy needle 210 is readily freed from the mechanical needle support assembly 200.

It is also preferred, that the needle support arm 230 and/or associated detectors generate position signals indicative of its movement. For example, a detector incorporated in each of the multiple joints and/or segments optionally senses an amount of rotation for that joint or amount of expansion/retraction for that segment. From a starting position, determining the amount of rotation in each joint and expansion/retraction in each segment then determines the location and orientation of the needle support arm 230 in relation to that starting position. Consequently, the movement of the needle support arm 230 and connected biopsy needle 210 is readily determined.

Additionally, in an alternate embodiment, the force and moment measuring assembly 260 is omitted and the biopsy needle 210 attached, again via the quick release connection or coupling 270, to the end of the needle support arm 230. In this embodiment then, detectors associated with the joints and segments of the needle support arm 230 also sense resistance to their movements and generate signals responsive thereto. From these signals, the forces experienced by the biopsy needle 210 are calculated or otherwise determined to generate the force signals.

Ultimately, the generated force and moment signals and position signals are relayed back to the haptic needle simulator 250 also via physical cable or in a wireless fashion using an infrared link, radio communication, or the like. In response to the received feedback (i.e., force and moment signals and position signals), the haptic needle simulator 250 reflects or mimics the forces and motion experienced by the biopsy needle 210 in the joystick 252 by applying appropriate forces, moments, and/or resistance thereto. In this manner then, via the joystick 252, the interventionalist who is physically manipulating the joystick 252 receives the same tactile sensations and/or feels the forces and moments experienced by the biopsy needle 210 as if he were directly manipulating the biopsy needle 210. Moreover, the flexibility in location of the haptic needle simulator 250 makes it possible for an expert at a remote location, optionally even a distant hospital, to perform the procedure with the same tactile feedback as if he were manually handling the biopsy needle 210.

In one preferred embodiment, a needle guide 280 is attached to the mechanical needle support assembly 200. The needle guide 280 is a substantially rigid hollow tube or shaft having an inner diameter and/or other inside dimensions sized to receive the biopsy needle 210. The illustrated needle guide 280 is curved. However, in an alternate embodiment, it is straight. In the case of the curved needle guide 280, the biopsy needle 210 used therewith is flexible in order to navigate the bend, and the bend is gradual in order to reduce friction between the biopsy needle 210 and inside walls of the needle guide 280 as the biopsy needle 210 progresses through the needle guide 280. In either case, curved or straight, it is preferred that the needle guide 280 or at least its inside walls are made from a low coefficient of friction material consistent with medical use. Moreover, the fit of the biopsy needle 210 within in the needle guide 280 is such that the biopsy needle 210 is freely advanced and/or retracted longitudinally therethrough, but without significant lateral play. In this manner then, the biopsy needle 210 has minimal frictional forces acting thereon, so that the forces experienced by the manipulator of the biopsy needle 210, either via the needle simulator 250 or via direct manipulation, is substantially the same as if no needle guide is involved in the procedure.

The advantage of employing a curved needle guide 280 is twofold. In the first instance, the curved needle guide 280 allows the mechanics (i.e., the needle support assembly 200, etc.) of the image-guided needle biopsy system 10 to be displaced from the site of needle insertion and image plane. Consequently, the mechanics of the system do not interfere with imaging. In the second instance, a curved needle guide 280 keeps the interventionalist's hands out of the beam of radiation 122 in situations where the interventionalist desires to attend to the procedure manually. This is an important feature in light of the fact that radiation exposure is a serious risk for interventionalists who regularly perform such procedures.

Placement of the needle guide 280 determines the insertion location and ensures the orientation or trajectory of the biopsy needle 210 insomuch as the biopsy needle 210 is constrained to only be advanced and/or retracted longitudinally therethrough. The needle guide's attachment to the needle support assembly 200 allows the needle guide 280 to be arbitrarily placed, oriented, and/or fixed with respect to the subject 20. In the illustrated embodiment, the needle guide 280 is attached to the needle support assembly 200 via an adjustable mechanical linkage 282 connected to a segment of the needle support arm 230. Alternately, the linkage 282 connects the needle guide 280 directly to the arch support assembly 220. In addition, the linkage 282 includes a quick release connection or coupling 284 so that, if desired, the needle guide 280 is readily disengaged from the needle support assembly 200.

In a preferred embodiment, the image-guided needle biopsy system 10 also includes an augmented feedback feature as well as a warning feature incorporated in an indicator panel 300 which also receives the same signals received by the haptic needle simulator 250. As with the haptic needle simulator 250, the indicator panel 300 optionally receives the feedback via physical cable, infrared link, radio communication, or the like. The indicator panel 300 includes a combination of visual and/or audible indicators which are triggered or controlled upon the detection of a predetermined or otherwise defined condition. For example, an audible indicator (e.g., a speaker, an acoustic transducer, etc.) has its volume or other acoustic characteristic controlled in response to the amount of axial force experienced by the biopsy needle 210. This feedback then augments the tactile feedback received by the interventionalist and gives the interventionalist an additional indication of the forces exerted on the biopsy needle 210. In terms of a warning, an audible alarm may sound to alert the interventionalist if the biopsy needle 210 hits bone. Optionally, that determination is made when a force signal exceeds an acceptable threshold. Alternately, the indicators are visual, such as flashing or steady state light emitting diodes (LEDs) of various patterns and/or colors. Additionally, the control panel 300 contains an alarm which is triggered if the system is not calibrated properly or not functioning. This safety feature prevents potential physical harm to the subject 20 due to failures in the system.

In addition, in a preferred embodiment, the image-guided needle biopsy system 10 contains a depth fail-safe feature which prevent over insertion of the biopsy needle 210. This optionally takes the form of mechanical stop 400 attached to the biopsy needle 210. The mechanical stop 400 abuts an end the needle guide 280 when the biopsy needle 210 is inserted to the desired depth thereby preventing further insertion. This feature is particularly valuable for procedures near critical areas, such as the spine or heart. The mechanical stop 400 is set for variable depths depending on the region of the subject 20 in which the procedure is being performed. In an alternate embodiment, stops are incorporated in the joints and segments of the needle support arm 230 to prevent over extension thereof. In yet another alternate embodiment, electronic controls limit the amount of insertion.

Another fail-safe feature optionally incorporated in the image-guided needle biopsy system 10 guards against subject injury caused by an unwanted shifting of the subject 20. Under these circumstances, the subject 20 may be injured when the biopsy needle 210 is not free to move with the subject 20. Accordingly, to reduce this risk, both quick release connections or couplings 270 and 284 are made to automatically disengage and/or separate when subjected to a shear force or pressure greater than an acceptable threshold.

There are many advantages in the present image-guided needle biopsy system 10 over biopsy systems and devices disclosed in the prior art. In the prior art, if an interventionalist wants to enjoy the benefits of real-time needle guidance via CCT imaging or fluoroscopy, the interventionalist typically exposes his hands to a potentially toxic dose of radiation over the course of several procedures. In contrast, the current image-guided needle biopsy system 10 allows the interventionalist to enjoy the advantages of real-time imaging without the risk of radiation exposure. This is true even where the interventionalist wishes to manually override the mechanical system and perform the procedure by hand. Use of the curved needle guide 300 still allows the interventionalist to keep his hands outside of the beam of radiation 122.

The image-guided needle biopsy system 10 of the present invention also allows for a more comfortable working environment for the interventionalist. In performing a needle biopsy manually, an interventionalist must often lean over the subject 20 in order to access the desired insertion point and/or orientation. This can be particularly troublesome in the case of larger subjects. In any event, leaning over the subject 20 in this manner potentially results in discomfort for the interventionalist and/or it may tend to cause him to be unsteady. In contrast, the image-guided needle biopsy system 10 in accordance with embodiments of the present invention, is easily manipulated by the interventionalist in a comfortable environment. The interventionalist may sit at one of the biopsy tables 240 on which rests the needle simulator 250, or he may sit in another room altogether. Either way, his arm is more readily supported in the proper manner to promote stability and comfort, and thereby, accuracy is enhanced. It is important to note that this increased stability and comfort do not come at the price of reduced tactile sensation or feel. Because of the force-reflecting haptic aspect of the needle simulator 250, the interventionalist enjoys the same tactile sensation, feel, and/or feedback as does an interventionalist performing the procedure manually.

Use of the image-guided needle biopsy system 10 also promotes a more sterile environment for the biopsy. Having fewer people come in contact with a subject 20 reduces the risk of infection. Therefore, with proper sterilization of the biopsy needle 210 and other components in near proximity to the site, the procedure is readily performed in a very sterile environment with a low likelihood of contamination.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or equivalents thereof.

Having thus described the preferred embodiments, the invention is now claimed to be:

1. A needle biopsy system comprising:
   a biopsy needle;
   a needle support assembly that holds the biopsy needle and manipulates the biopsy needle in response to received control signals;
   a force measuring transducer associated with the needle support assembly for measuring forces experienced by the biopsy needle; and,
   a needle simulator having an input device, said needle simulator generating the control signals in response to manipulation of the input device by an operator, said operator receiving feedback from the transducer in accordance with the forces experienced by the biopsy needle.

2. The needle biopsy system according to claim 1, wherein the feedback received by the operator comprises tactile sensations experienced by the operator as the operator manipulates the input device, said tactile sensations mimicking those the operator would have received had the operator directly manipulated the biopsy needle.

3. The needle biopsy system according to claim 1, wherein the force measuring transducer includes:
   a load cell connected to the biopsy needle, said load cell generating force signals in response to detected forces acting on the biopsy needle, said force signals being relayed to the needle simulator.

4. The needle biopsy system according to claim 3, wherein the load cell also generates moment signals in response to moments acting on the biopsy needle, said moment signals being relayed to the needle simulator.

5. The needle biopsy system according to claim 1, wherein prior to the needle support assembly manipulating the biopsy needle, the control signals are filtered to compensate for unwanted manipulations of the input device by the operator.

6. The needle biopsy system according to claim 1, wherein said needle biopsy system further includes:
   an image guidance system comprising a medical diagnostic imager having a human viewable display which is employed to visualize procedures.

7. The needle biopsy system according to claim 1, wherein needle biopsy system further comprises:
   an indicator panel having at least one of a visual and an audible signal controlled in response to the forces experienced by the biopsy needle and perceivable by the operator.

8. A needle biopsy system comprising:
   a biopsy needle;
   a needle support assembly that holds the biopsy needle and manipulates the biopsy needle in response to received control signals;
   a needle guide attached to the needle support assembly, said needle guide comprising a hollow shaft dimensioned to receive the biopsy needle such that the biopsy needle freely progresses longitudinally therethrough while restricting the needle's lateral movement; and
   a needle simulator having an input device, said needle simulator generating the control signals in response to manipulation of the input device by an operator, said operator receiving feedback from the transducer in accordance with the forces experienced by the biopsy needle.

9. The needle biopsy system according to claim 8, wherein the hollow shaft is curved.

10. The needle biopsy system according to claim 8, wherein the biopsy needle is connected to the needle support assembly via a quick release coupling arranged such that the biopsy needle is readily detachable from the needle support assembly.

11. The needle biopsy system according to claim 10, wherein the quick release coupling automatically releases the biopsy needle from the needle support assembly upon application of an amount of force thereto in excess of a determined level.

12. A method for performing a needle biopsy on a subject, said method comprising:
   (a) adjusting a needle support assembly which holds a biopsy needle such that the biopsy needle is positioned relative to the subject at a desired insertion point and orientation;
   (b) manipulating an input of a needle simulator remote from said needle support assembly in order to effect a desired manipulation of the biopsy needle;
   (c) generating a needle control signal in response to the manipulation of the input of the needle simulator;
   (d) relaying the needle control signal to the needle support assembly;
   (e) producing the desired manipulation of the biopsy needle in response to the needle control signal;
   (f) sensing a force on the biopsy needle;
   (g) generating a force signal in response to the sensed force on the biopsy needle;
   (h) relaying the force signal to the needle simulator; and,
   (i) applying tactile feedback to the input of the needle simulator in response to the force signal.

13. The method according to claim 12, wherein the tactile feedback mimics tactile sensations which would have been felt had the biopsy needle been manipulated directly.

14. The method according to claim 12, wherein between steps (c) and (e) the method further comprises:

filtering the control signal to compensate for unwanted components of the manipulation of the input of the needle simulator.

15. The method according to claim 12, wherein during the needle biopsy said method further comprises:

obtaining medical diagnostic images of a region of interest of the subject, said region of interest having the biopsy needle located therein.

16. The method according to claim 12, wherein the method further comprises:

providing a human perceivable signal in response to the force signal.

17. The method according to claim 16, wherein the human perceivable signal is an alarm which is triggered when the force signal crosses a determined threshold.

18. An image-guided needle biopsy system, said system comprising:

a CCT imaging unit having a subject support for suspending a subject at least partially within an examination region;

a biopsy needle; and a mechanical needle biopsy system, said mechanical needle biopsy system comprising:

a robotic arm adjustably mounted to said subject support, said robotic arm inserting and retracting the biopsy needle into and out of the subject and sensing forces acting on the biopsy needle;

a needle guide through which the biopsy needle is directed, said needle guide being detachably mounted to the robotic arm; and, a haptic needle simulator that is manipulated in order to control the biopsy needle remotely, said haptic needle simulator reflecting sensed forces acting on the biopsy needle to an interventionalist manipulating the haptic needle simulator.

19. The image-guided needle biopsy system according to claim 18, wherein the biopsy needle is flexible and the needle guide is curved.

20. The image-guided needle biopsy system according to claim 18, wherein the biopsy needle is detachably coupled to the robotic arm.

* * * * *